(12) United States Patent
Takahashi

(10) Patent No.: US 7,101,334 B2
(45) Date of Patent: Sep. 5, 2006

(54) OPTICAL OBSERVATION DEVICE AND 3-D IMAGE INPUT OPTICAL SYSTEM THEREFOR

(75) Inventor: Susumu Takahashi, Iruma (JP)

(73) Assignee: Olympus Corporation, Tokyo (JP)

( * ) Notice: Subject to any disclaimer, the term of this patent is extended or adjusted under 35 U.S.C. 154(b) by 398 days.

(21) Appl. No.: 10/279,715

(22) Filed: Oct. 25, 2002

(65) Prior Publication Data

US 2003/0083551 A1    May 1, 2003

(30) Foreign Application Priority Data

Oct. 31, 2001    (JP)    ............................ 2001-334057

(51) Int. Cl.
A61B 1/06        (2006.01)
A61B 1/04        (2006.01)
H04N 15/00       (2006.01)
H04N 13/02       (2006.01)

(52) U.S. Cl. ...................... 600/166; 600/111; 600/171; 348/45; 348/49

(58) Field of Classification Search ................. 348/42, 348/47, 49, 45, 58; 600/111, 166; 359/377–378, 359/464–465; 353/8
See application file for complete search history.

(56) References Cited

U.S. PATENT DOCUMENTS

| | | | | |
|---|---|---|---|---|
| 2,255,631 A | * | 9/1941 | Schulman | ................... 359/377 |
| 2,811,077 A | * | 10/1957 | Wiemer et al. | ................. 353/8 |
| 4,480,893 A | * | 11/1984 | Fantone | ...................... 359/465 |
| 4,895,431 A | * | 1/1990 | Tsujiuchi et al. | .............. 359/29 |
| 5,003,385 A | * | 3/1991 | Sudo | ........................... 348/49 |
| 5,142,357 A | * | 8/1992 | Lipton et al. | .................. 348/48 |
| 5,313,306 A | * | 5/1994 | Kuban et al. | ................. 348/65 |
| 5,432,543 A | * | 7/1995 | Hasegawa et al. | ............. 348/45 |
| 5,557,454 A | | 9/1996 | Takahashi | |
| 5,588,948 A | | 12/1996 | Takahashi et al. | |
| 5,689,365 A | * | 11/1997 | Takahashi | .................... 359/362 |
| 5,720,706 A | | 2/1998 | Takahashi et al. | |
| 5,743,846 A | * | 4/1998 | Takahashi et al. | .......... 600/166 |
| 5,743,847 A | * | 4/1998 | Nakamura et al. | .......... 600/166 |
| 5,749,362 A | * | 5/1998 | Funda et al. | ................. 600/407 |
| 5,776,050 A | * | 7/1998 | Chen et al. | .................. 600/117 |
| 6,063,023 A | | 5/2000 | Sakiyama et al. | |
| 6,139,490 A | * | 10/2000 | Breidenthal et al. | ......... 600/111 |
| 6,154,315 A | | 11/2000 | Street | |
| 6,198,484 B1 | * | 3/2001 | Kameyama | .................. 345/419 |
| 6,417,880 B1 | * | 7/2002 | Uomori et al. | ................ 348/42 |
| 6,430,224 B1 | * | 8/2002 | Naito et al. | ............. 375/240.16 |
| 6,466,255 B1 | * | 10/2002 | Kagita et al. | .................. 348/42 |
| 6,473,206 B1 | * | 10/2002 | Fujimoto et al. | ........... 358/497 |
| 6,692,432 B1 | * | 2/2004 | Yarush et al. | ................ 600/179 |

* cited by examiner

*Primary Examiner*—John Leubecker
*Assistant Examiner*—Philip R. Smith
(74) *Attorney, Agent, or Firm*—Arnold International; Bruce Y. Arnold

(57) ABSTRACT

An optical observation device for observing 3-D images of an endoscope is disclosed. The optical observation device includes: an image input means having a rod-shaped front part with a sufficiently small diameter for insertion within a living human being, the rod-shaped front part containing a front optical system for capturing images having parallax in a direction that includes a component in the longitudinal direction of the rod-shaped front part; a means for detecting at least one of the parallax direction or parallax magnitude of the front optical system; an image conversion means for changing at least one of the parallax direction or parallax magnitude of images received from the image input means so as to form converted images; and a 3-D image observation means for enabling the 3-D observation of the converted images.

14 Claims, 18 Drawing Sheets

OPTICAL OBSERVATION DEVICE AND 3-D IMAGE INPUT OPTICAL SYSTEM THEREFOR

BACKGROUND OF THE INVENTION

Currently, endoscopes or surgical microscopes are extensively used in mildly invasive surgery, but are less commonly used for complex surgical techniques. However, techniques for employing endoscopes or surgical microscopes in more complex surgery have been proposed and are now under development. In these techniques, an image sensor detects images of an object which are then displayed on a display unit while a manipulator is operated to perform microscopic surgery. Prior art optical observation devices for use in surgery include an optical observation device that combines a pupil-separation-type, rigid endoscope with a 3-D observation unit, as disclosed in Japanese Patent Publication No. H06-59199 (corresponding to U.S. Pat. Nos. 5,588,948, and 5,720,706), and in Japanese Patent Publication No. H06-202006 (corresponding to U.S. Pat. No. 5,557,454).

As shown in FIG. 18(a), the pupil-separation-type, rigid endoscope used in such an optical device may be formed of, for example, a rigid part 51 for insertion and a holder part 52 that is connected to the rigid part 51. The rigid part 51 is formed of, in order from the object side, an objective lens 53 having plural lens elements and a relay lens 54 having plural lens groups. The objective lens 53 and the relay lens 54 form an image input optical system which transmits images of object to a beam splitter. The holder part 52 contains a diaphragm 55 containing two apertures 55a, 55b for separating the light transmitted via the image input optical system. Prisms 56, 56' are used to then direct the light of the right and left light beams, respectively, so as to convey right and left images, respectively. The prisms 56, 56' have reflecting surfaces 56a, 56'a that are inclined at a 45° angle to the optical axis. These prisms 56, 56' reflect the right and left light beams, respectively, that enter them via the two apertures 55a, 55b in the diaphragm 55, which is positioned normal to the optical axis. The holder part 52 contains prisms 57, 57' having reflecting surfaces that reflect the right and left light beams which have been separated by being reflected 90 degrees by the prisms 56, 56', respectively, so as to be incident onto lenses 58, 58', respectively, and image sensors such as CCDs 59, 59', respectively. The CCDs 59, 59' are positioned at the image planes of the lenses 58, 58' and they convert the right and left object images, respectively, into electric signals so that the right and left images can be displayed on a monitor via a control unit (not shown).

The imaging optical system S, which includes the holder part 52 as well as the above-discussed components from the apertures 55a, 55b to the CCDs 59, 59', is rotated as a unit in relation to the rigid part 51. As shown in FIG. 18(b), such a pupil-separation-type, rigid endoscope has a small parallax that is determined by the distance d between the optical axes. The distance d is approximately one-fourth to one-eighth the outer diameter D of the relay lens 54. When such a pupil-separation-type, rigid endoscope is modified for providing a perspective view by making the leading end I of the rigid part 51 shown in FIG. 18(a) have a slanted orientation in relation to the longitudinal direction of the rigid part 51, the imaging optical system S can then be rotated according to the perspective view direction of the leading end I so as to properly orient the image.

The two apertures 55a, 55b formed in the diaphragm 55 can be variable in spacing so as to adjust the parallax magnitude for comfortable observation. Such prior art optical observation devices for use in surgery also include an optical observation device that combines a dual-optical-system-type, rigid endoscope with a 3-D observation unit as disclosed in Japanese Patent Publication No. H06-59199 (which corresponds in subject matter to U.S. Pat. Nos. 5,588,948 and 5,720,706). As shown in FIG. 19(a), the dual-optical-system-type, rigid endoscope used in such optical devices includes, for example, a rigid part 61 for insertion and a holder part 62 that is connected to the rigid part 61. The rigid part 61 contains two image input optical systems 65, 65' formed of, in order from the object side, objective lenses 63, 63', each formed of plural lens elements, and relay lenses 64, 64', each formed of plural lens groups. The holder part 62 includes the following for forming respective object images that are transmitted via each of the two image input optical systems 65, 65': imaging optical systems formed of prisms 66, 66' and 67, 67', imaging lenses 68, 68', and CCD's 69, 69'. The CCDs 69, 69' convert the object images transmitted via the two image input optical systems 65, 65' into electric signals in order to display them on a monitor via a control unit (not shown). Such a dual-optical-system-type, rigid endoscope provides a larger parallax d (FIG. 19(b)) than the pupil-separation-type, rigid endoscope with d being equal to, in this case, approximately one-half the diameter D of the space reserved for the optical system.

Referring back to the pupil-separation-type, rigid endoscope as shown in FIGS. 18(a) and 18(b), although images can be correctly oriented in such a device, there exists a problem in that sufficient parallax magnitude can not be ensured. On the other hand, the dual-optical-system-type, rigid endoscope as is shown in FIG. 19(a) also has some disadvantages. Although the parallax magnitude can be made sufficiently large, the parallax magnitude as well as the parallax direction are fixed. Thus, neither the parallax magnitude nor the parallax direction may be readily adjusted. However, a large parallax may be excessive for some close-up observations, and having the image orientation fixed causes an inconvenience in that images with proper perspective can not be ensured.

BRIEF SUMMARY OF THE INVENTION

The present invention relates to an optical observation device for use in surgery and a 3-D image input optical system for use with the optical observation device. More particularly, the present invention relates to optical observation devices for use in surgery Such as rigid endoscopes and surgical microscopes in which images of an object are formed using an image sensor and are then observed using an image observation unit. Also, the invention relates to a 3-D image input optical system for use with the optical observation device.

The objects of the present invention are to provide:

a 3-D image observation optical device in which a sufficient parallax magnitude is ensured and in which images can be correctly oriented, and a 3-D image input optical system for use therewith;

a 3-D image observation optical device in which a rod-shaped, insertable portion is fixed in orientation and images can be correctly oriented in conjunction with an optical system having a parallax direction, and a 3-D image input optical system for use therewith;

a 3-D image observation optical device that provides viewers with an observation capability having an optimized parallax magnitude, and a 3-D image input optical system for use therewith; and a 3-D image observation optical device in which the rod-shaped, insertable portion is fixed and the amount of parallax can be increased or decreased in conjunction with an optical system having a similar parallax magnitude, and a 3-D image input optical system for use therewith.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

Figure 1:
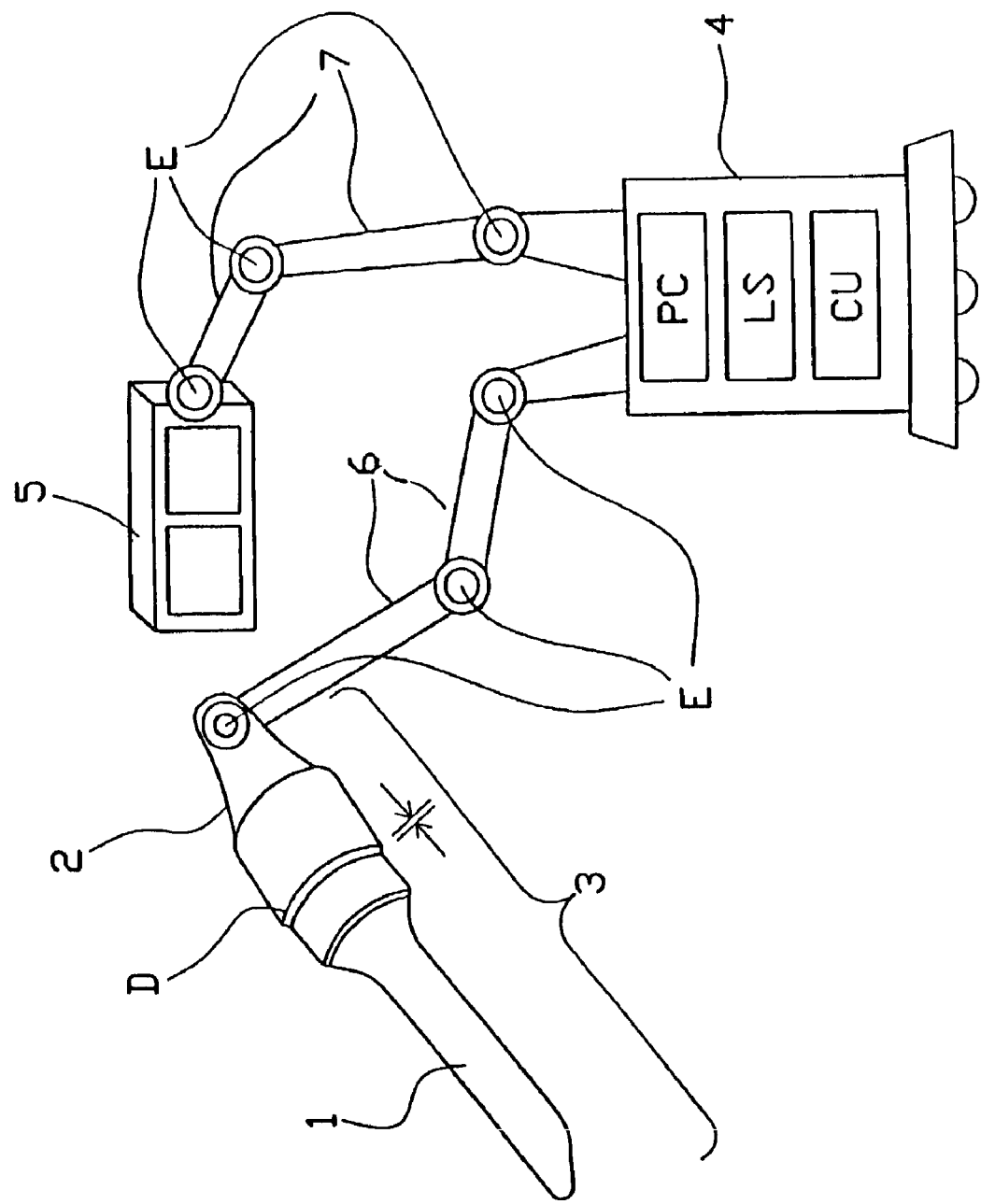
FIG. 1 shows the configuration of components of an optical observation device according to Embodiment 1 of the present invention.

A 3-D image input optical system according to the present invention for use in an optical observation device includes an optical system having a rod-shaped optical input part at a foremost position. Two light paths from the object, having parallax, enter the rod-shaped input part and are combined into a single light path by a polarization surface. Light traveling along one of the optical paths is transmitted at the polarization surface, reflected on a prism surface and then, when incident the second time on the polarization surface, has its p-component transmitted through the polarization surface in a direction not of interest and its s-component reflected along a common path to a positive lens. Light traveling along the other optical path is reflected from one or more prism surfaces and then has its s-component reflected in a direction not of interest and its p-component transmitted along the common path by the polarization surface. The optical axes of the two light paths as they are incident the input part are parallel to each other and lie in either the perspective view direction or side view direction in relation to the longitudinal direction of the rod-shaped, optical input part.

The optical observation device of the present invention includes an image input device which provides at least two images having parallax, an electronic image conversion device for changing the parallax direction of images to one that is different from the parallax direction of the image input device, and a 3-D image observation device for enabling 3-D observation of the images output from the image conversion device. Alternative to, or in addition to, changing the parallax direction, the image conversion device may change the parallax magnitude of images from the image input device.

According to a first feature of the invention, an optical system may be employed in which the parallax direction is fixed but a large amount of parallax is ensured. According to a second feature of the invention, where a sufficient parallax is difficult to achieve using a single optical axis because of using an optical system two optical axes are positioned so as to achieve a parallax component along the direction of insertion of the endoscope.

A device for changing the parallax direction that uses an image processing operation may be provided so as to convert the parallax direction of images to coincide with a parallax direction of a 3-D observation device, so that images having a proper parallax may be observed using the 3-D observation device. In order to accomplish this, a device for detecting the parallax direction of the image input device is provided, and images are automatically rotated so as to have the correct parallax direction with respect to an observer using the 3-D observation device.

According to a second feature of the invention, an image input optical system having a fixed parallax magnitude is combined with an image conversion device for increasing/decreasing the parallax magnitude of images. A device for measuring the amount of parallax of the images is provided and the measured parallax is used to change parallax (increase/decrease) coefficients, which are then used to fix the amount of parallax at an appropriate value. The converted images are then displayed on a 3-D image display device, ensuring an image observation with an appropriate parallax magnitude as well as an appropriate parallax direction.

EMBODIMENT 1

FIG. 1 shows the entire configuration of the optical observation device of Embodiment 1 of the invention. The optical observation device of this embodiment is formed of an image input device 3 that includes a rod-shaped, insertable portion 1 and a front holder part 2, a holder body 4, an image display 5, and rotatable supports 6, 7. The insertable portion 1 has an end with a diameter small enough to be insertable within a living human being and the other end is held by the front holder part 2. An optical system for capturing images having parallax is provided in the insertable portion 1. Within the front holder part 2 is a TV camera.

The image input device 3 is held to the holder body 4 by the rotatable supports 6. The image input device 3 is separable at part D in the figure into an insertable portion 1 and a front holder part 2. The holder body 4 contains a light source unit LS, a TV camera control unit CU, and a computer PC for image conversion processing. The image display 5 is held to the holder body 4 by rotatable supports 7.

Figure 2A:
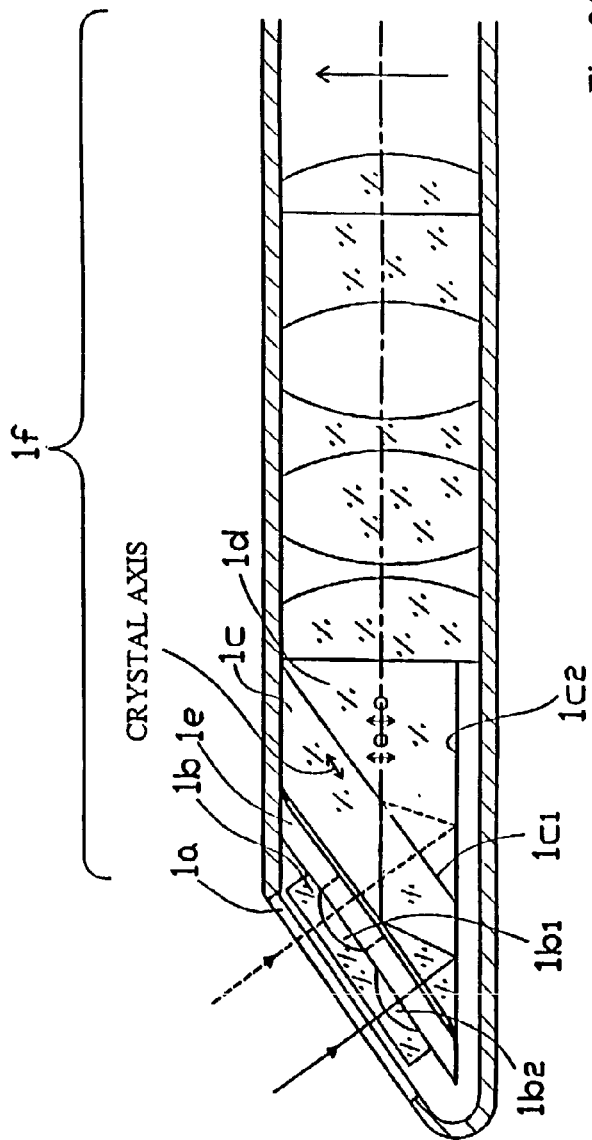
FIGS. 2(a) and 2(b) show the front optical system 1f of the optical observation device of Embodiment 1, with FIG. 2(a) being a sectional view along the longitudinal direction, and FIG. 2(b) being a top plan view which shows the leading end surface.
Figure 2B:
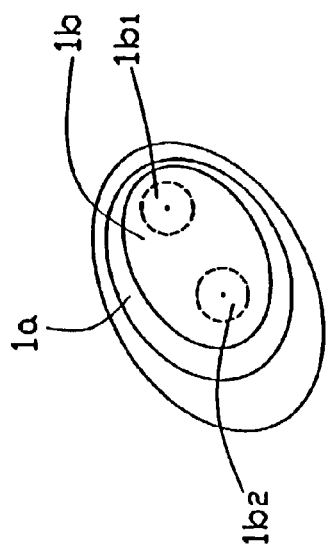

In the optical observation device of Embodiment 1, as shown in FIG. 2(*a*), the rod-shaped, insertable portion has an end surface that is slanted in relation to the longitudinal direction of the rod-shaped, insertable portion so as to form a perspective view observation system. Near this slanted region, a lens 1*b* of negative refractive power having two concave surfaces 1*b*1, 1*b*2 is provided so as to accommodate two parallel optical paths within part of the insertable portion. In this way, a larger parallax may be achieved (or, alternatively, a smaller diameter lens can be provided having the same parallax). A cover glass 1*a* is also shown in FIGS. 2(*a*) and 2(*b*).

Referring to FIG. 2(*a*), two light paths, of unpolarized light traveling in the direction from an object being observed having two perspectives are illustrated with one path being shown using a broken line and the lower path being shown using a solid line. Referring to the light that travels along the solid line, both the s and p-components enter the prism 1*c* and are twice reflected. However, at the surface 1*c*1, the s-component is refracted out of the illustrated light path and only the p-component is transmitted.

Referring to the light that travels along the broken line, both the s-component light and the p-component light enter the prism 1*c* and each component is transmitted on the first incidence with surface 1*c*1. Both components are then internally reflected at the lower surface 1*c*2 and are incident once more at surface 1*c*1. At this point, the s-component light is reflected along the illustrated light path and the p-component light is transmitted by the surface 1*c*1 away from the illustrated light path. Thus, to the right of the surface 1*c*1, the p-component light carries images that enter the cover glass 1*a* along the light path shown with a solid line, and the s-component light carries images that enter the cover glass 1*a* along the light path shown with a broken line.

An object may be illuminated by an illumination light emitted from the light source LS via an illumination optical system (not shown in the figure). Cover glass 1*a* forms an optical input surface.

In the optical observation device of Embodiment 1, two images having parallax as well as different polarization components are made to be coaxial so that the full space reserved for the optical system in the insertable portion can be utilized. These images are relayed along the insertable portion, and are then separated so as to follow separate optical paths. This enables the relayed images to have a high quality. As shown in FIG. 2(*a*), the image input device includes within the insertable portion, prism optical systems 1*c* and 1*d*, the boundary surface of which has a separation surface 1*c*1 that transmits/reflects light, depending on its polarization, in order to combine onto a single light path two separated light beams of different polarization. Light from the object is transmitted/reflected at the separation surface 1*c*1 depending on its polarization so as to form input images of the object having parallax, with at least some of the parallax being in the longitudinal direction of the insertable portion 1. In more detail, the prism optical system 1*c* is made of crystal material with its crystal axis parallel to the boundary surface.

A parallel plate 1*e* is also shown in FIG. 2(*a*) in which an aperture is formed in one of the optical paths so that two optical paths have the same length. The structure in FIG. 2(*a*) ensures a parallax (the distance between the two optical axes) that is 0.6 times the lens outer diameter of the rod-shaped, insertable portion.

Figure 3:
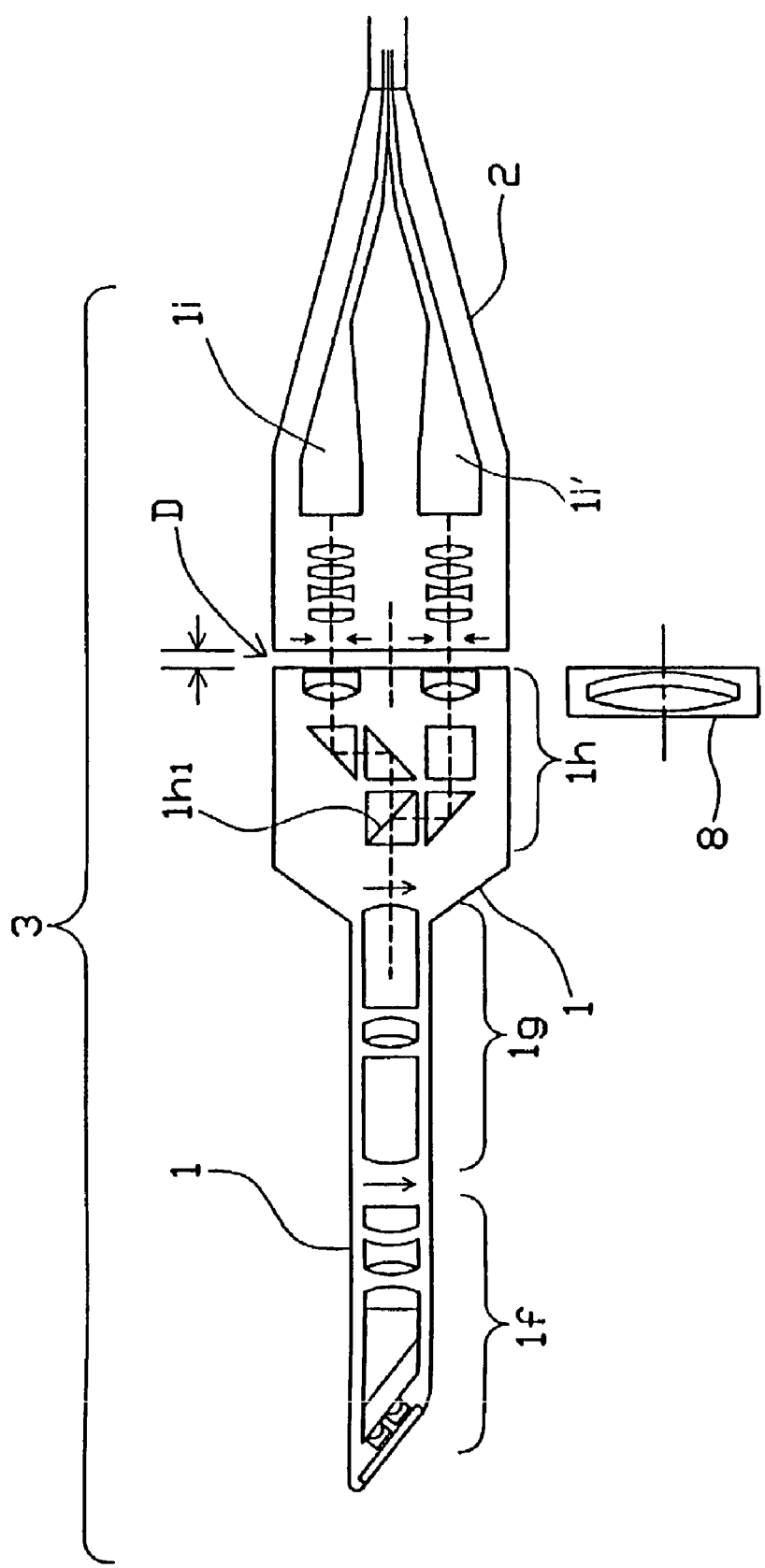
FIG. 3 is a sectional view of the entire optical system of the image input device 3.

FIG. 3 is a sectional view of the entire optical system provided in the image input device 3 of the optical observation device of Embodiment 1. The image input device 3 has a structure in which two images having parallax and that enter the front objective optical system 1*f* are combined using a polarization surface so as to transit a common optical path with different polarization and are relayed by the relay optical system 1*g*. The light is then separated into two images depending on its polarization by a polarization and separation optical system 1*h*. The two images having parallax are then formed onto respective TV cameras 1*i*, 1*i*′.

In FIG. 3, light is reflected at, or transmitted through, a polarizing surface 1*h*$_1$, depending on its polarization. The polarization and separation optical system 1*h* is formed of a prism having a polarizing surface 1*h*$_1$, as well as various prisms and lenses for guiding the light that has been separated by the polarizing surface 1*h*$_1$ into two light beams having different polarizations along respective optical paths. In addition, the image input device 3 of Embodiment 1 is separable at part D in the figure into the rod-shaped, insertable portion 1 and the front holder part 2 in which TV cameras 1*i*, 1*i*′ are provided. An objective lens 8 can be connected to the front holder part 2 in place of the insertable portion, enabling a conventional microscope to be mounted to the front holder part 2 for microscopic observation.

Figure 4:
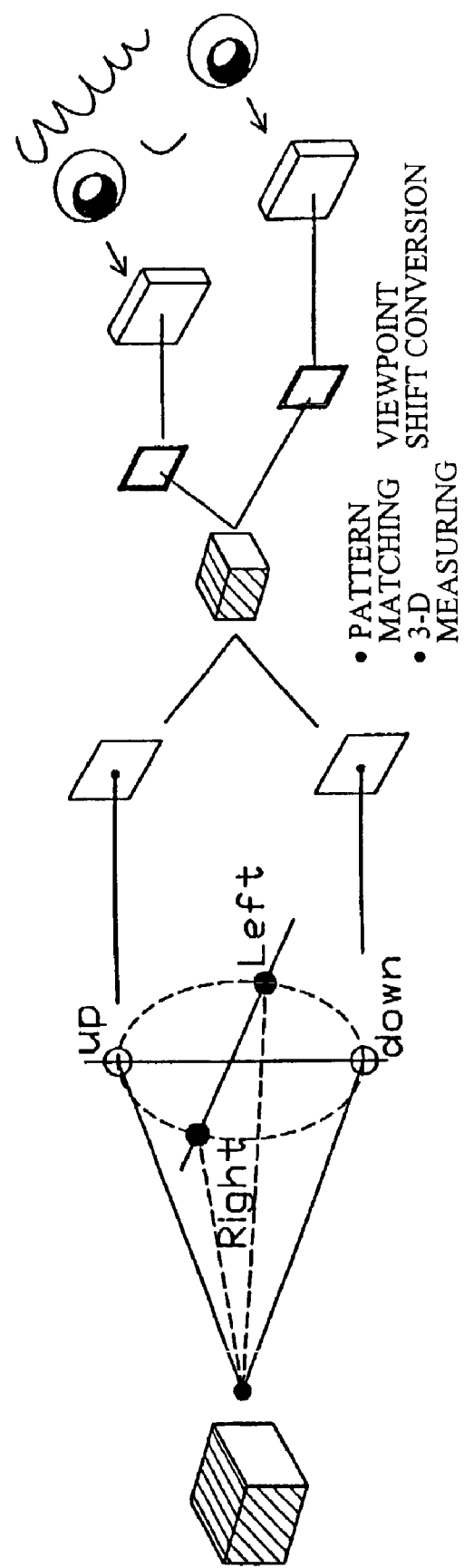
FIG. 4 is a schematic diagram of a parallax direction conversion apparatus used in the optical observation device of Embodiment 1.

FIG. 4 is a schematic presentation of the parallax direction conversion device used in the optical observation device of Embodiment 1. In Embodiment 1, when the rod-shaped, insertable portion is placed with the parallax direction horizontal to the viewer, the parallax direction is aligned with that of the viewer, allowing a 3-D observation. However, when the rod-shaped, insertable portion is placed with the parallax direction vertical to the viewer, the parallax direction is rotated 90° relative to the viewer. Thus, the viewer is not presented with a view suitable for 3-D observations. The present invention solves this problem by providing an image conversion device for changing the parallax direction.

The device for changing the parallax direction of the images in the optical observation device of Embodiment 1 performs the following procedures using a computer PC provided in the holder body 4. Both images are always shifted in the parallax direction. Therefore, with both images, the corresponding points of the right and left images in the scanning line direction are detected and a calculation is performed to obtain the positional shift magnitude of the right and left images, expressed in pixels. A technique for locating the corresponding image points is called pattern matching. An example of this technique is disclosed in Japanese Patent Publication No. H10-248806 (which corresponds in subject matter to U.S. Pat. No. 6,063,023, which is hereby incorporated by reference).

Figure 5B:
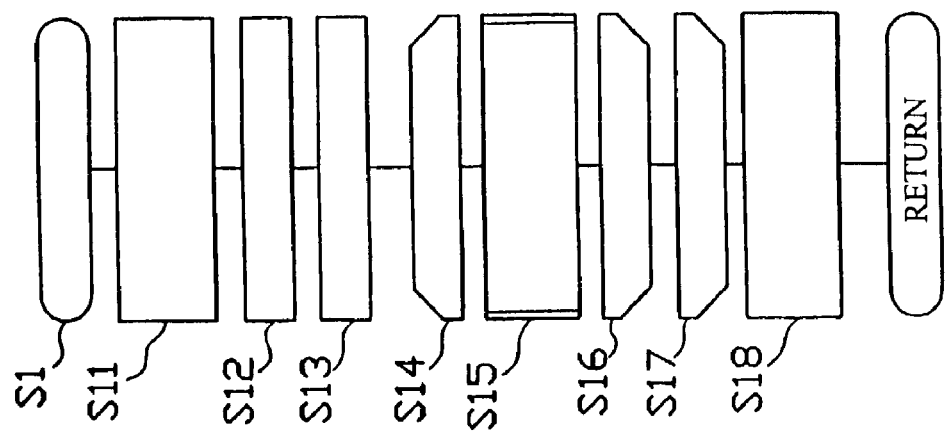
FIGS. 5(a) and 5(b) are flowcharts to show examples of pattern matching in the image parallax direction conversion apparatus of Embodiment 1, with FIG. 5(a) being a flowchart of the 3-D coordinate analysis procedure, and FIG. 5(b) being a flowchart of the pattern matching procedure.
Figure 5A:
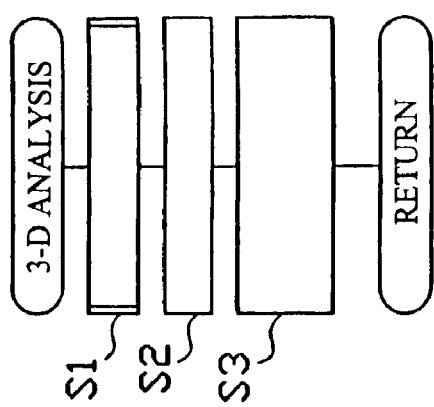

FIG. 5(*a*) shows a flowchart of pattern matching. First, a subroutine is run to detect the matching points, i.e. the corresponding points of the two, right and left, images (stereo images) (Step S1). A shift magnitude between the right and left images is then calculated using the coordinates of the corresponding points (Step S2). Then, the 3-D coordinates of the point in question are calculated and the routine ends (Step S3).

Figure 6:
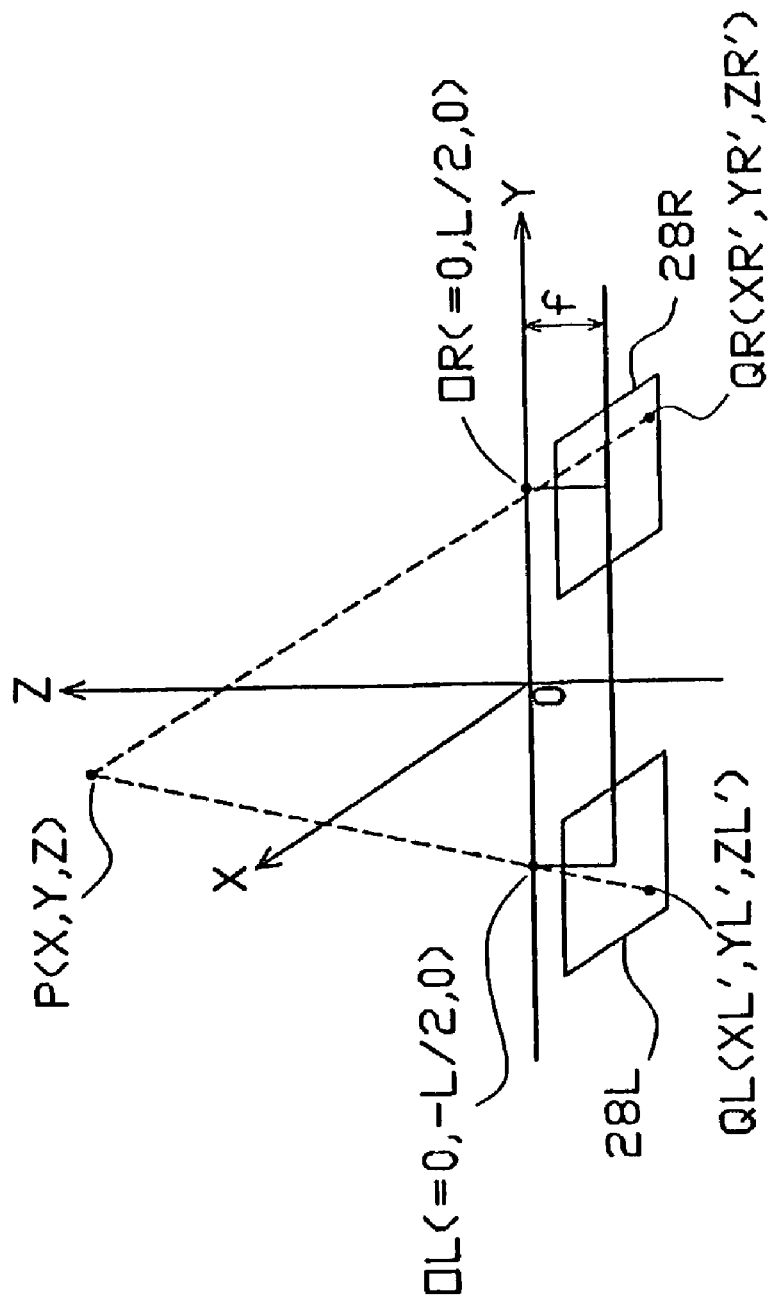
FIG. 6 shows the positional relationship between the right and left images on a 3-D coordinate system having x, y, and z axes.

The principle of the 3-D coordinate analysis procedure in the subroutine above will now be explained with reference to FIG. 6. FIG. 6 shows the positional relationship of two, right and left, images on a 3-D coordinate system having an x, y, and z axis. The images of the object P are formed on the right and left image planes 28R and 28L of an image sensor element. The optical system has pupils at OR and OL, a focal length f, and image points QR, QL. The distance between the points OR and OL is assumed to be L. The following two equalities may be derived from the line QR-OR:

$$x/xR' = \{y-(L/2)\}/\{yR'-(L/2)\} = z/(-f) \quad \text{Equation (1)}$$

The following two equalities may also be derived from the line QL-OL:

$$x/xL' = \{y+(L/2)\}/\{yL'+(L/2)\} = z/(-f) \quad \text{Equation (2)}$$

The above two pairs of equalities may be readily solved to obtain x, y, and z, i.e., the 3-D coordinates of the point P.

The pattern matching procedure performed in the subroutine of the Step 1 of the 3-D coordinate analysis procedure of FIG. 5(*a*) will now be explained with reference to FIG. 5(*b*). First, a pattern area is condensed to determine the pattern size for the pattern matching (Step S11). The pattern is set according to the value of k (Step S12). Here, the pattern area is 36×36 pixels for k=1; is 24×24 pixels for k=2; and is 12×12 pixels for k=3.

Changing the value of k from a small to large number leads to the condensing area changing from a large area to a small area, and thus improves the precision of detection of the corresponding points.

Next, in Step S13, the search range is determined. In other words, the pattern search region of the right image is determined.

In Steps S14–S16, pattern matching is performed for the determined search range. This pattern matching uses a normalized cross-correlation to detect the corresponding point. The largest coordinate (X, Y) of the normalized cross-correlation function is considered to be the corresponding point.

In Step S17, the value k is increased and the pattern area is condensed for the new k in order to detect the corresponding point.

In Step S18, the matching point is determined. At this point, the values of the normalized cross-correlation function can be displayed on a monitor for use as a reference of reliability. When the normalized cross-correlation function shows values (within a range from 0 to 1) that are smaller than a predetermined value, a manual matching procedure can be performed. A positional shift map of the right and left images is then created by performing the above procedure for all pixels.

The normalized cross-correlation function M (u, v) that is used for pattern matching, as discussed above, has the following conventional expression:

$$M(u,v) = \left[\sum_S\sum(f(x+u,y+v)-f')(t(x,y)-t')\right] \Bigg/ \left[\sum_S\sum(f(x+u,y+v)-f')^2 \times \sum_S\sum(t(x,y)-t')^2\right]^{1/2} \quad \text{Equation (3)}$$

where
t(x, y) is a template,
f(x, y) is image data,
t' is the average brightness of the template, and
f' is the average brightness of images.

Figure 7:
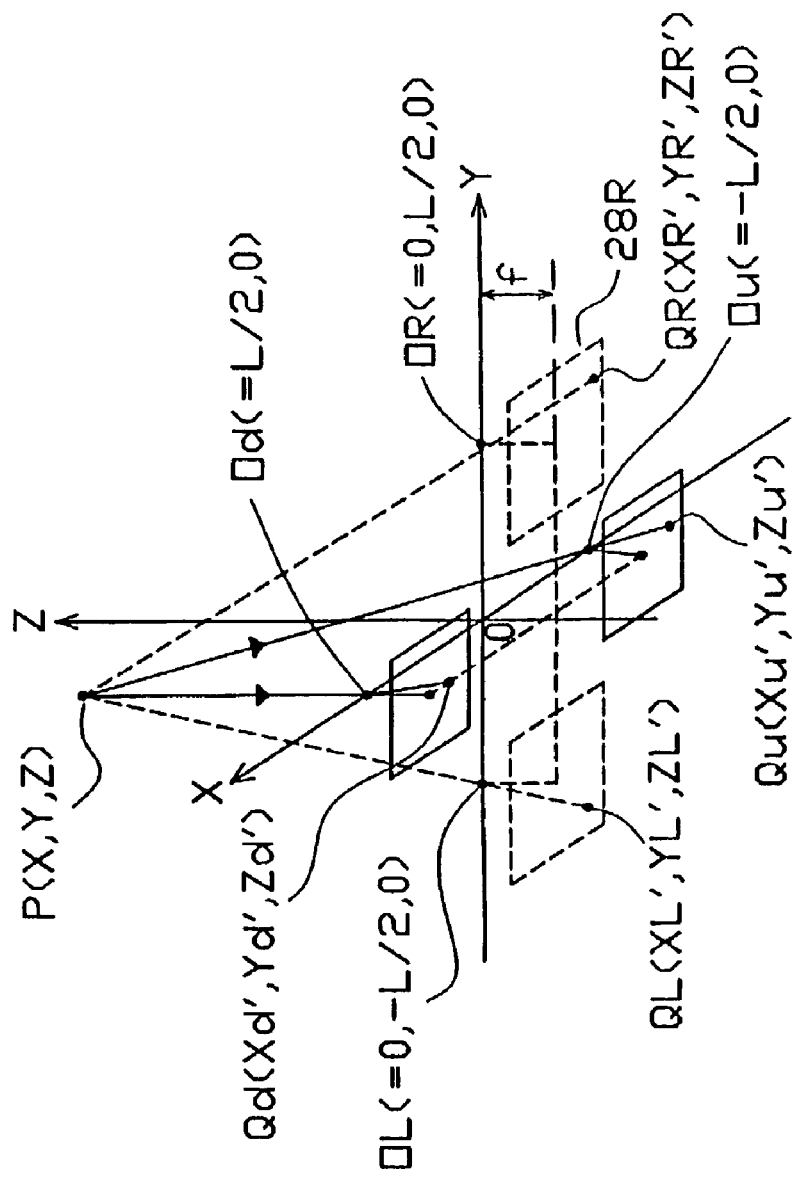
FIG. 7 illustrates viewpoint conversion for the right and left images shown in FIG. 6.

Next, viewpoint conversion is performed using a positional shift map. The conversion process will now be explained with reference to FIG. 7. Referring to FIG. 7, if the distance between the right and left optical axes of the optical system is known, a concave-convex magnitude may be calculated using a positional shift magnitude. The distance L between the viewpoints is known. The corresponding points Qu and Qd are used to calculate a 3-D position P(X, Y, Z). At this point, a 3-D map of the object is produced.

Then, because the coordinate position of the parallax conversion is known (for instance, the parallax conversion in this case involves a 90° rotation), images can be projected onto a coordinate as seen from a particular direction so as to obtain converted 3-D images that are seen from a different viewpoint. In this case, the point P(X, Y, Z) is projected onto the coordinates QL and QR which have the same inter-viewpoint distance L.

In Embodiment 1, the orientations of the insertable portion 1 and the observation device are detected by the encoders E provided on the rotatable supports 6, 7 shown in FIG. 1. By successively renewing images for the converted viewpoint, the observation device enables the images to be observed with a correct parallax. In the embodiment above, the parallax direction is altered 90°. However, the projected coordinate positions can be appropriately altered for successively rotated positions.

Figure 8:
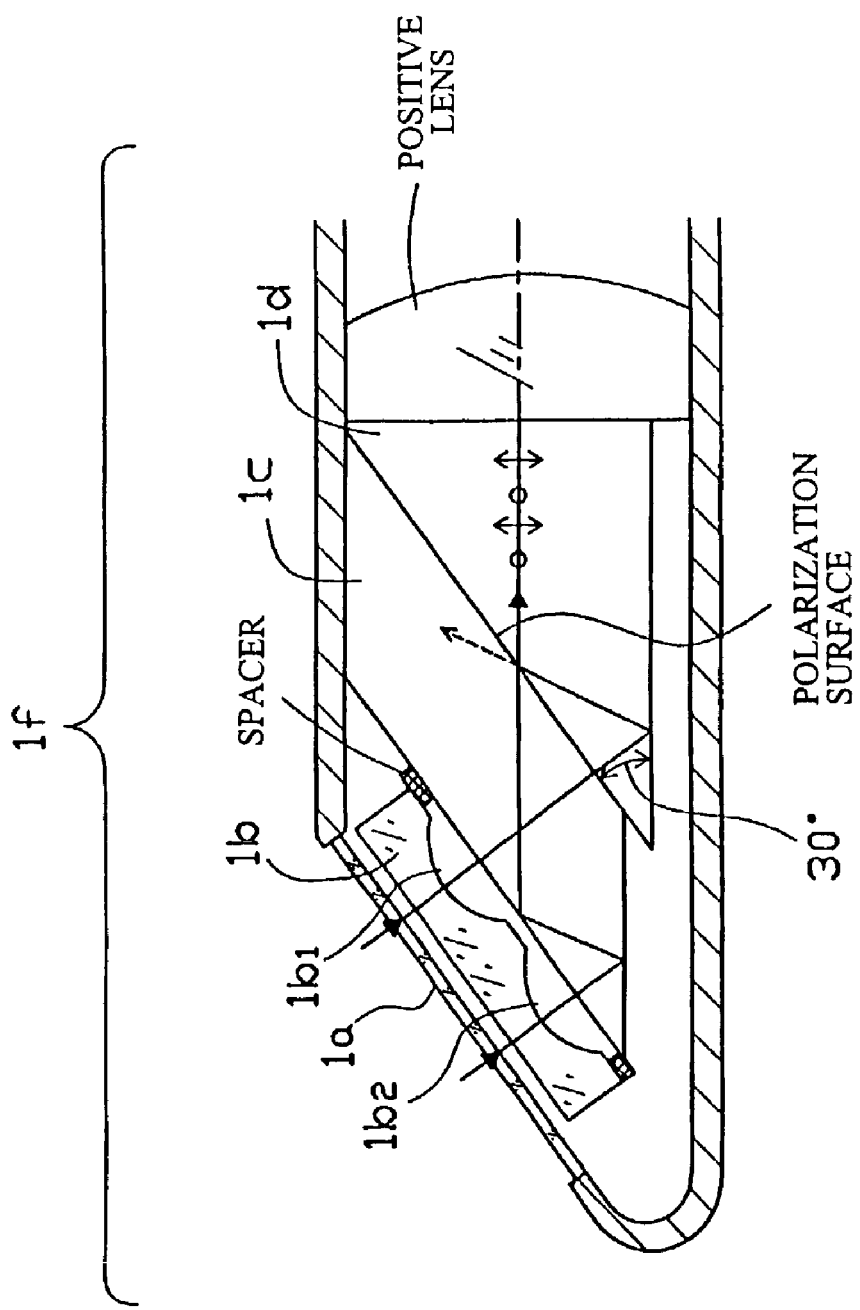
FIG. 8 is a sectional view of a modified version of the front objective optical system 1f shown in FIG. 2.

FIGS. 8 to 11 show possible modifications to the front objective optical system 1*f* of Embodiment 1 as shown in FIG. 2. The rod-shaped, insertable portion that includes the front objective optical system 1*f* has the same structure as is shown in FIG. 2. In FIG. 8, the front objective optical system 1*f* has a perspective view angle of 60°. A boundary surface between prisms 1*c*, 1*d* has a polarization surface that transmits/reflects light depending on its polarization components so as to combine into a single optical pain light from two separate optical paths having different polarizations. An object is illuminated by the light emitted from the light source LS for illumination via an illumination optical system (not shown in the figure). The reflected light from the object follows the respective optical paths, is combined to a common optical path, and is then separated so as to yield a 3-D image. The parallax magnitude (i.e., the distance between the optical axes) is approximately one-half the outer diameter of the lens. Generally, the lens is designed to have an outer diameter from 1 mm to 10 mm. In FIG. 8, the two prisms are formed of an optical medium so that the index of refraction is the same for both prisms, and a polarizing membrane is provided on the interface between the two prisms. Light entering from the object side follows paths similar to that described previously for FIG. 2(*a*) so that, to the right of a polarization surface (positioned between the prisms 1*c* and 1*d*), light having s-polarization is light that has entered through concave surface 1*b*1 and light of p-polarization is light that has entered through the concave surface 1*b*2. Thus, once again, within a combined light path to the right of a polarization surface, the p-component light carries images that enter the cover glass 1*a* along the light path shown with a solid line, and the s-component light carries images that enter the cover glass 1*a* along the light path shown with a broken line.

Figure 9:
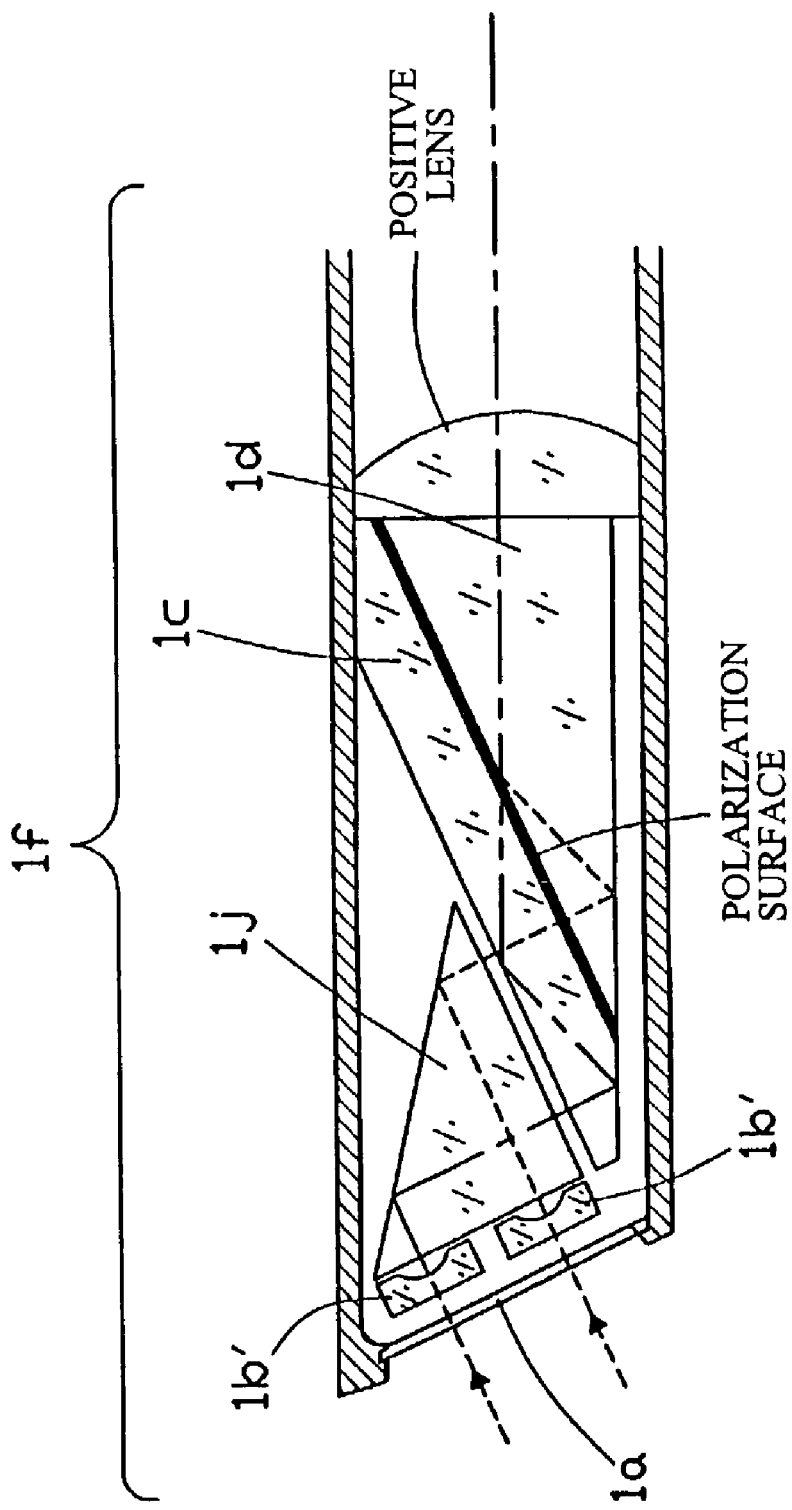
FIG. 9 is a sectional view of another modified version of the front objective optical system 1f shown in FIG. 2.

In FIG. 9, the front objective optical system 1*f* has a perspective view angle of 30°. As in FIG. 8, the boundary surface between the prisms 1*c*, 1*d* has a polarization surface that transmits or reflects light depending on its polarization so as to combine two input optical paths into a single common optical path. The prism 1*c* can be made of birefringent material. In the embodiment of FIG. 9, each optical path has a lens 1*b'*, as illustrated. Another prism 1*j* having a reflecting surface is also shown in FIG. 9.

Figure 10:
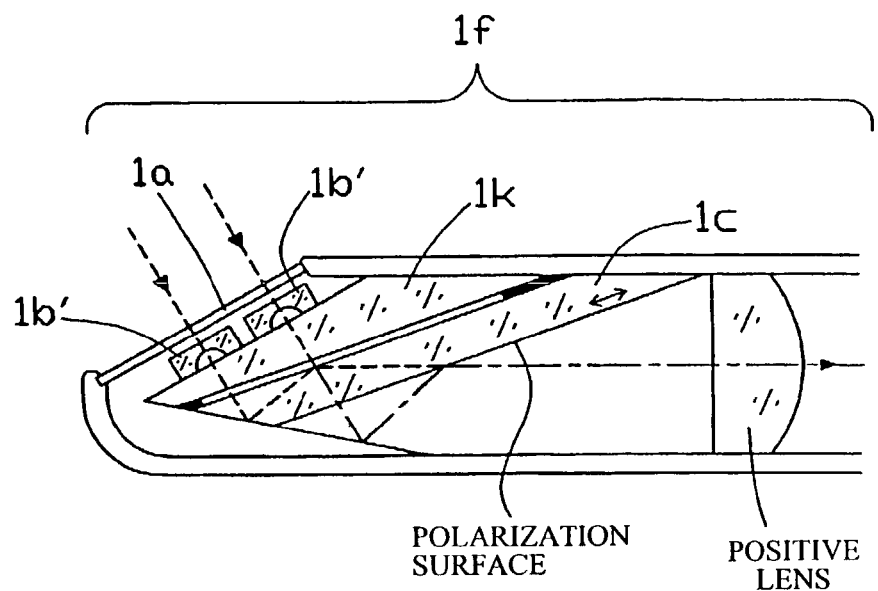
FIG. 10 is a sectional view of another modified version of the front objective optical system 1f shown in FIG. 2.

In FIG. 10, the front objective optical system 1*f* has a perspective view angle of 70°. The boundary surface of the prism 1*c* facing the positive lens has a polarization surface that transmits or reflects light depending on its polarization components so as to guide light into two separate optical paths. Another prism 1*k* is also shown in FIG. 10.

Figure 11:
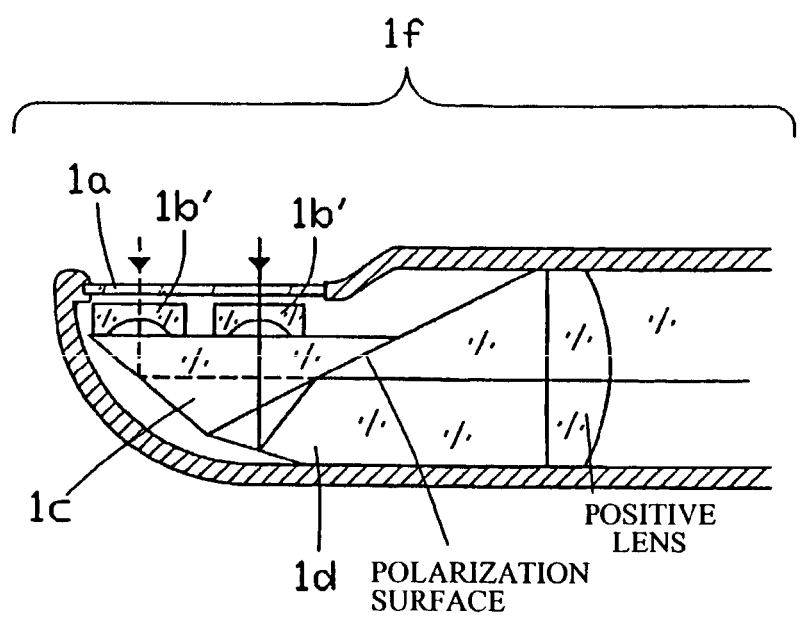
FIG. 11 is a sectional view of another modified version of the front objective optical system 1f shown in FIG. 2.

In FIG. 11, the front objective optical system 1*f* has a side view angle of 90°. As in FIG. 8, the boundary surface between the prisms 1*c*, 1*d* has a polarization surface that transmits or reflects light depending on its polarization component so as to combine two optical paths into a common optical path. The prisms 1*c*, 1*d* in FIG. 11 cause the light in the separate optical paths to undergo reflection a different number of times. Therefore, a computer image processor that is connected to the image input part, which is not shown in this figure, is used to perform an inversion process for images from one of the optical paths. Cover glass 1*a* forms an optical input surface.

Figure 12:
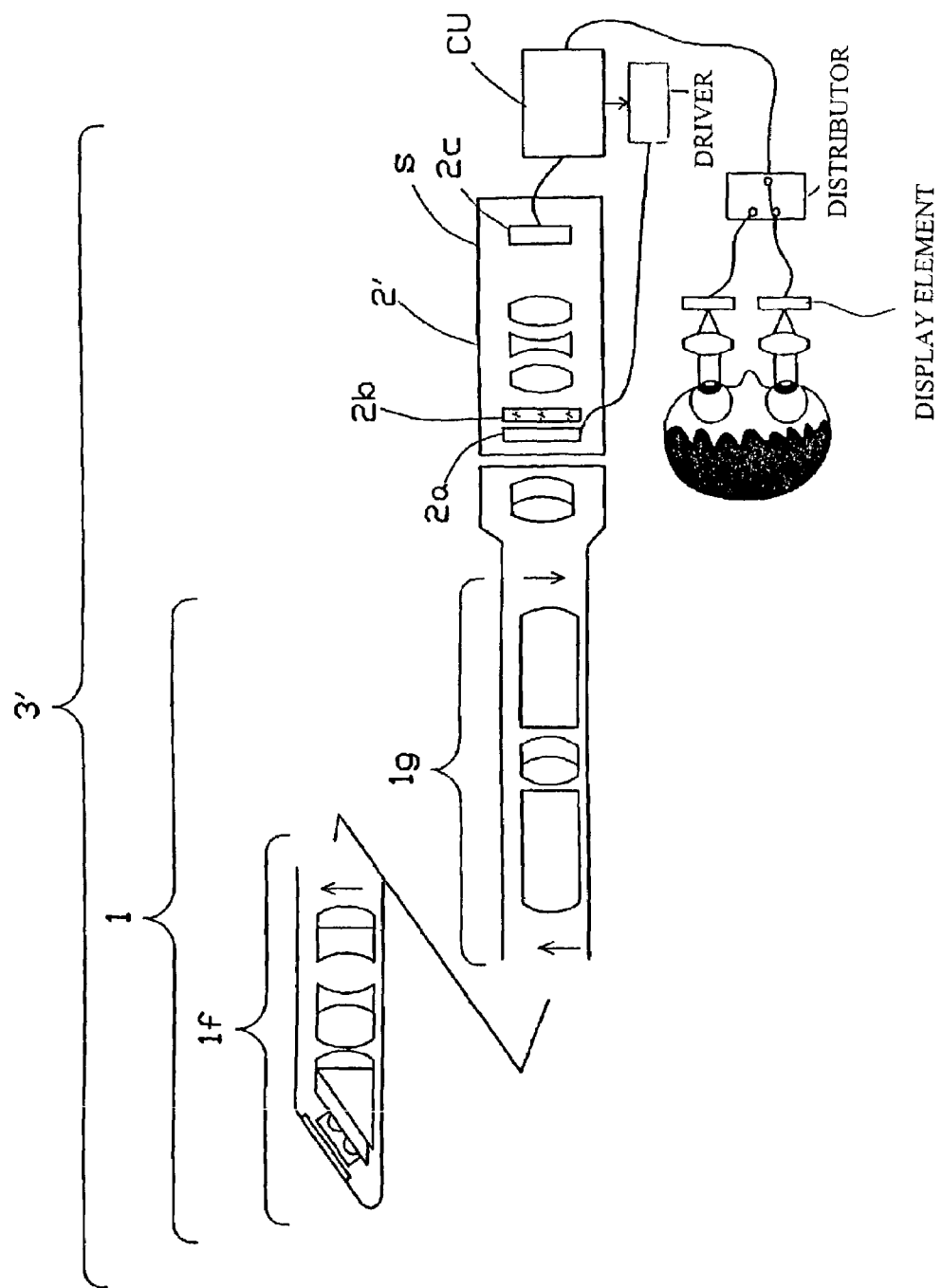
FIG. 12 shows an embodiment of the image input device 3' having a front optical part 1 that includes a front optical system 1f, and a front holder part 2' in which a TV camera is provided.

FIG. 12 shows an embodiment of the image input device 3' that includes the insertable part 1 having a front objective optical system 1*f* formed as in the embodiments above and a front holder part 2' in which a TV camera is provided. The front objective optical system 1*f* has any one of the structures of the embodiments described above. For the TV camera, a variable phase element 2*a* and analyzer 2*b* are provided in the front holder part 2'. The phase is alternated by 90° using the TV camera control unit CU and a driver so that images that are captured through the front objective optical system and which have parallax can be alternately observed through the one TV camera. A CCD 2*c* is also shown in FIG. 12. The TV camera control unit CU is connected to a distributor that is, in turn, connected to right and left display elements. Captured images having parallax are alternately displayed on the right and left display elements via the distributor that is synchronized with the driver in order to achieve 3-D observations.

Figures 13A, 13B:
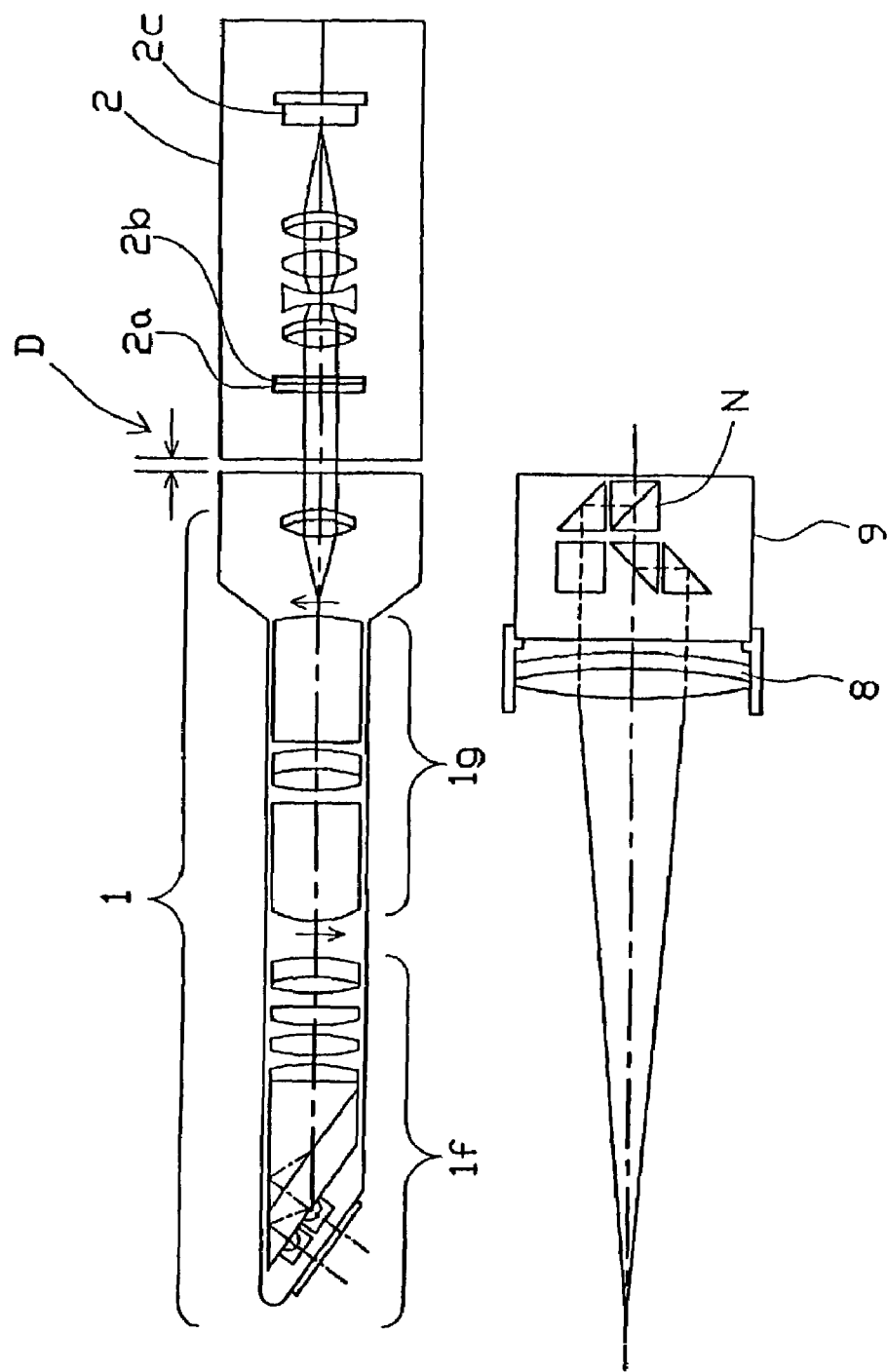
FIGS. 13(a) and 13(b) show, in sectional views, an embodiment in which either a rod-shaped, insertable portion 1 as shown in FIG. 13(a) or a conventional microscope objective lens 8 as shown in FIG. 13(b) may be exchangeably attached to the front holder part 2 as shown in FIG. 13(a)

FIGS. 13(*a*) and 13(*b*) show an embodiment of the image input device in which the rod-shaped, insertable portion 1 and a conventional microscope objective lens 8 are exchangeable in the optical observation device according to the present invention. An optical path merging part 9 comprising an optical element N for merging the optical paths having different polarization components is provided behind the objective lens 8. This allows 3-D observation in accordance with the TV camera operation shown in FIG. 12 when the objective lens 8 of FIG. 13(*b*) is attached to the front holder part 2 of FIG. 13(*a*).

Figure 19A:
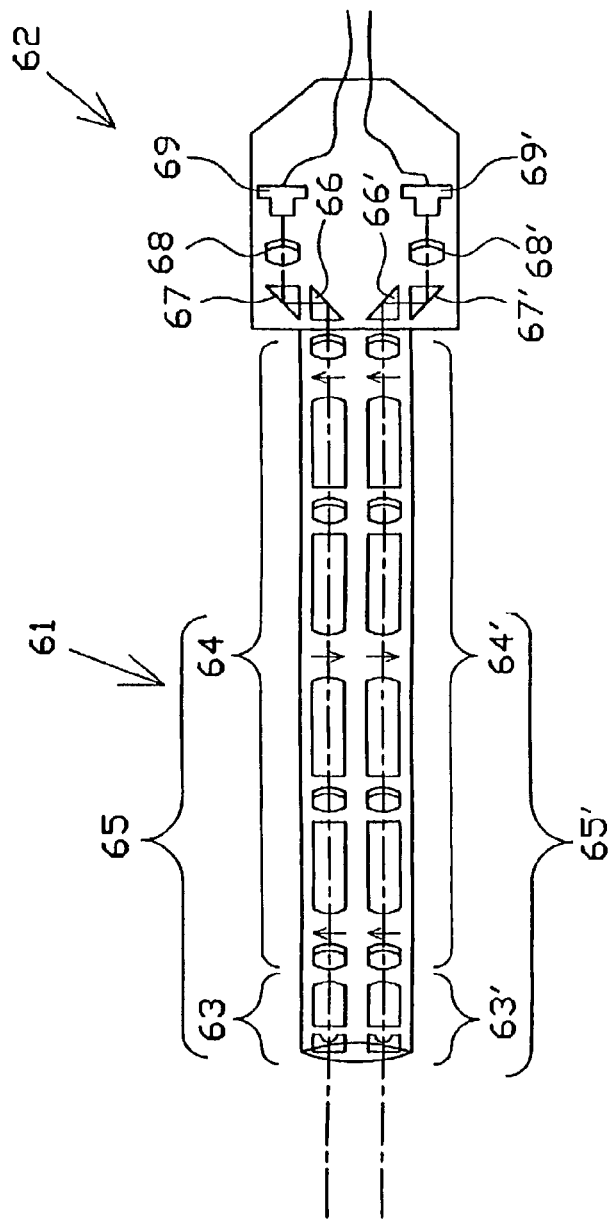
FIGS. 19(a) and 19(b) are side and front sectional views, respectively, of a prior art optical observation device that combines a dual-optical-system-type, rigid endoscope with a 3-D observation unit.
Figure 19B:
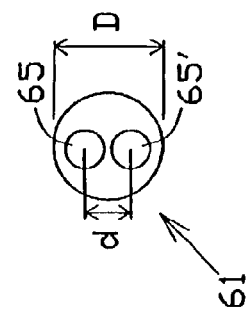

In the optical observation device of the above embodiments of the invention, the relay optical system 1*g* is not restricted to a single optical system and a combination of the front objective optical system 1*f* and two relay optical systems as in the prior art shown in FIG. 19 can be used. When two relay optical systems are used as in the prior art, the image input device can not convert the parallax direction on its own. The present invention uses each relay optical system in combination with its respective image conversion device, thereby realizing a parallax system in combination with its respective image conversion device, thereby realizing a parallax direction conversion.

Figure 18A:
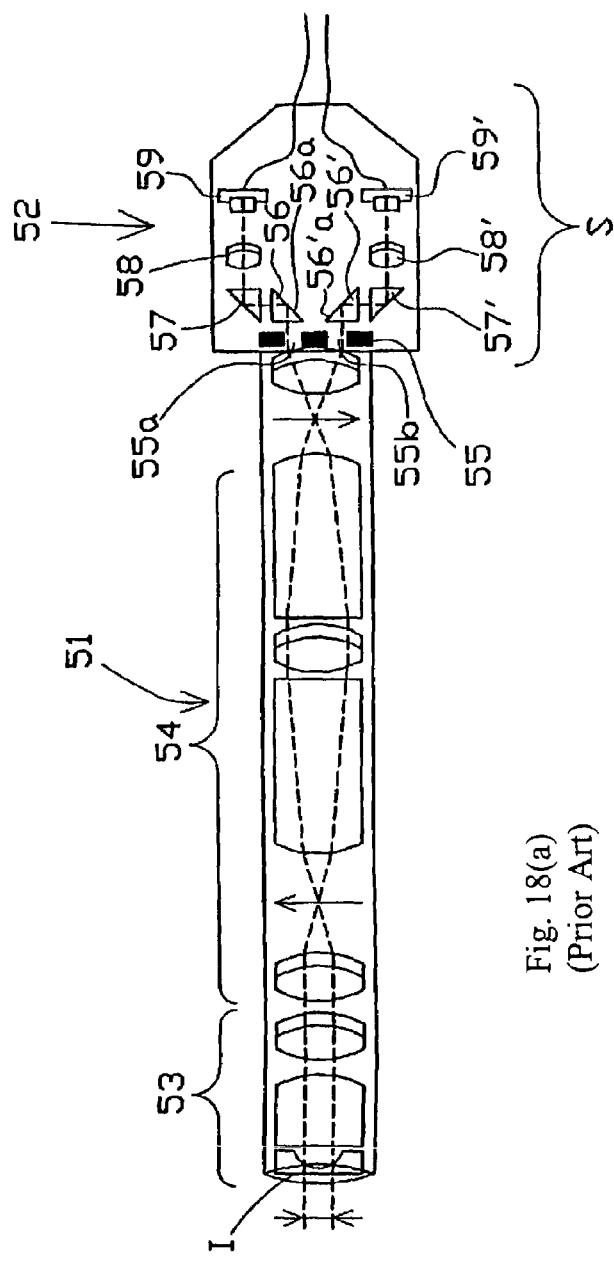
FIGS. 18(a) and 18(b) are side and front sectional views, respectively, of a prior art optical observation device that combines a pupil-separation-type, rigid endoscope with a 3-D observation unit.
Figure 18B:
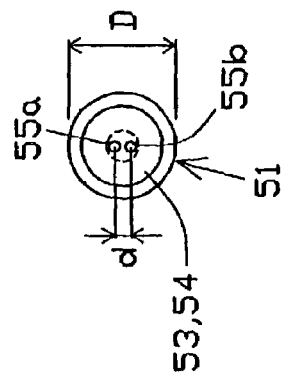

Parallax magnitude is optimized by pupil separation for some observation objects. Therefore, the invention uses a combination of the prior art pupil-separation-type optical system shown in FIG. 18 and the image viewpoint rotational conversion device. This can eliminate the relative rotation of the insertable portion 1 and TV camera part, thereby improving ease of operation and advantageously enhancing reliability due to the elimination of mechanical movements.

EMBODIMENT 2

Figure 14:
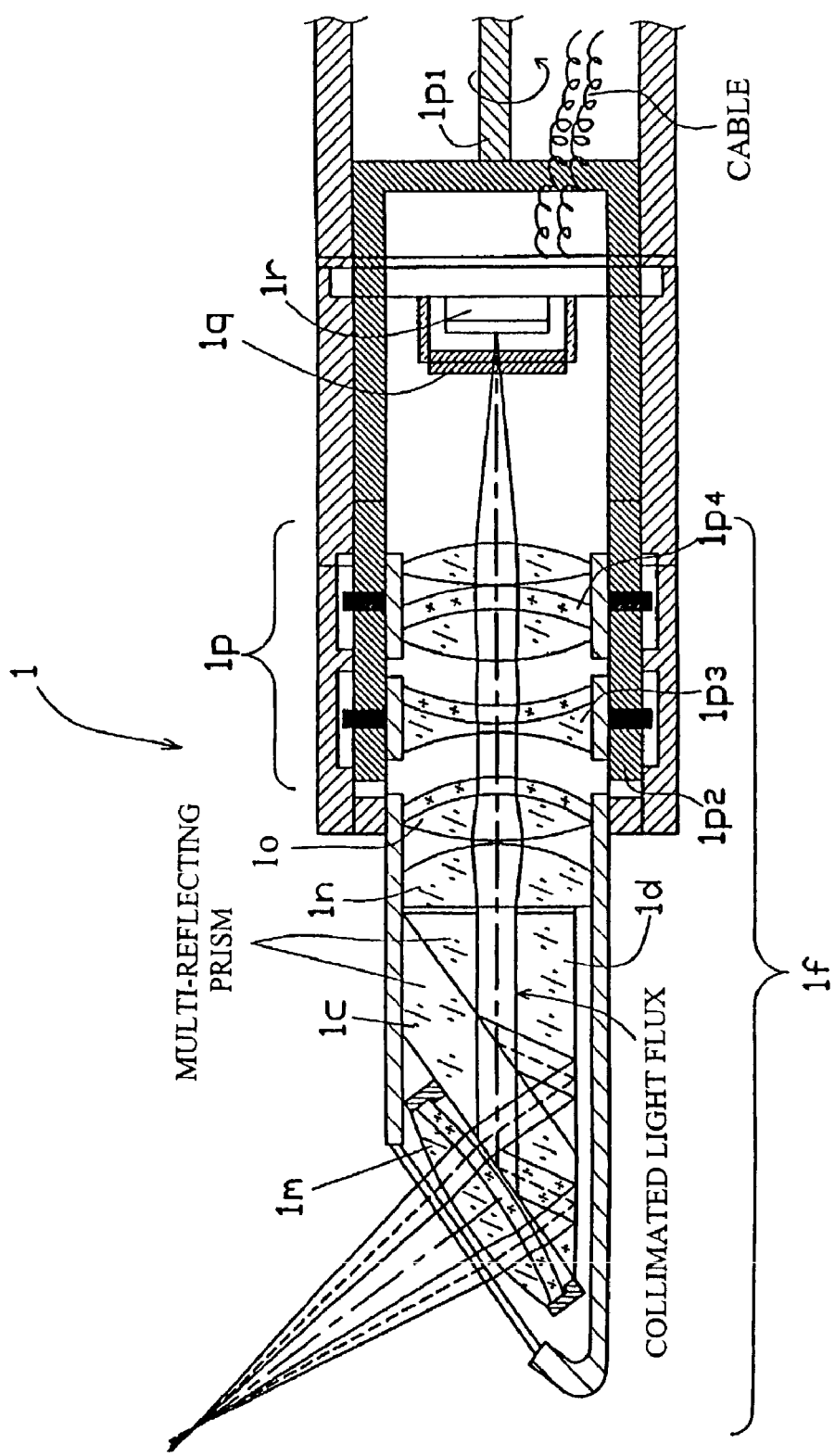
FIG. 14 is a sectional view of a rod-shaped, insertable portion 1 that is used in the optical device of Embodiment 2 of the present invention.

FIG. 14 is a sectional view of the rod-shaped, insertable portion 1 of an optical observation device according to Embodiment 2 of the invention. The insertable portion 1 is formed of an objective optical system 1*f*, a polarization switching element 1*q*, and an image sensor element 1*r*. The objective optical system 1*f* includes an objective lens 1*m*, prisms 1*c*, 1*d* having a boundary surface which is a polarizing surface, positive lenses 1*n*, 1*o*, and zoom/focus part 1*p*. The zoom/focus part 1*p* serves as a zoom lens. For zooming, a wire 1*p*1 extended from the back is rotated to move lens groups 1*p*3, 1*p*4 via a zoom cam 1*p*2 of the zoom lens. In Embodiment 2, the objective lens 1*m* is a biconvex lens which forms a collimated light flux. This is to avoid interference of the two optical paths with the lens frame, ensuring a maximized distance between the optical axes of the optical paths. A polarization switching element 1*q* is positioned before the image sensor element 1*r* for rotating the polarization direction by 90° in synchronism with the TV camera's image timing. This allows the image sensor element to read parallax images alternately and sequentially. Embodiment 2 is also provided with an electronic image conversion device and a 3-D image display device (not shown). Their operations are the same as described above for Embodiment 1, and thus further explanation will be omitted.

EMBODIMENT 3

Figure 15A:
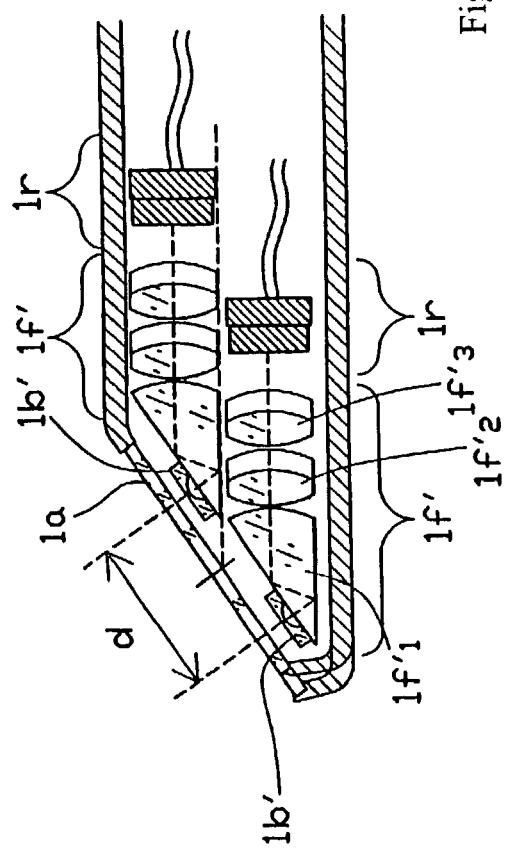
FIGS. 15(a) and 15(b) show a rod-shaped, insertable portion of an optical observation device of Embodiment 3 of the present invention, with FIG. 15(a) being a sectional view taken along the longitudinal direction and FIG. 15(b) being a top plan view that shows the leading end surface.
Figure 15B:
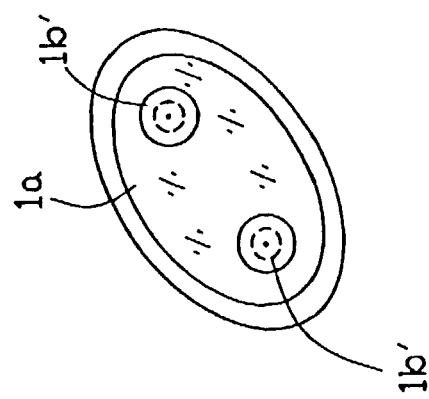

FIGS. 15(a) and 15(b) show the rod-shaped, insertable portion of the optical observation device of Embodiment 3 of the invention. The insertable portion of Embodiment 3 includes two longitudinal optical systems in which are positioned front objective optical systems 1f, 1f' and image sensor elements 1r, 1r. This allows a larger parallax as compared to the case of using a single objective optical system. The objective optical system 1f includes a lens 1b' of negative refractive power, a prism 1f1, a lens 1f2, and a lens 1f3. The objective optical system has a leading end with a perspective view angle of 60°, resulting in the cut end being twice as long as the case where an axial view but no perspective view is provided. This allows a larger parallax for the same diameter insertable part. Or, the diameter can be reduced so long as a sufficient magnitude of parallax is provided. Furthermore, the present invention combines the parallax direction conversion device as is described above. The optical observation device having the rod-shaped, insertable portion of Embodiment 3 also produces a large parallax and allows 3-D observation with a proper orientation corresponding to the parallax direction.

EMBODIMENT 4

Figure 16:
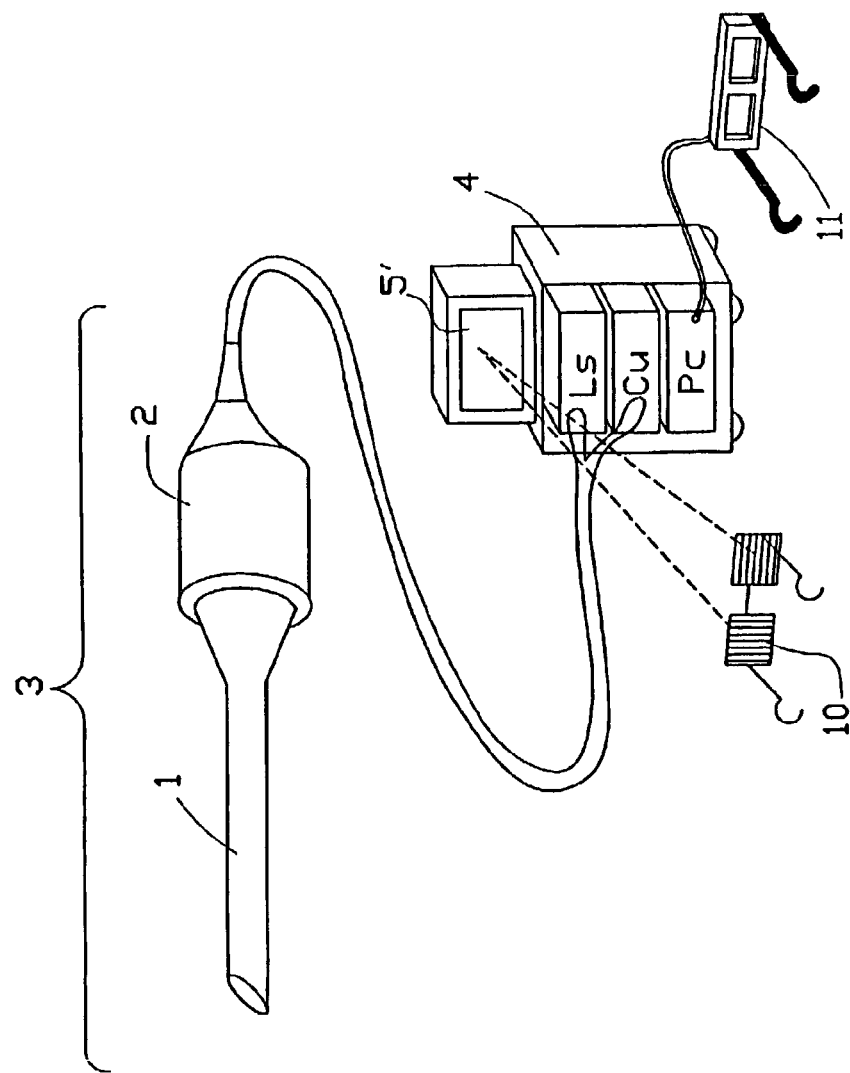
FIG. 16 shows the entire optical observation device of Embodiment 4 of the present invention.

FIG. 16 shows the entire configuration of the optical observation device of Embodiment 4 of the invention. The optical observation device of Embodiment 4 includes an image input device 3 that is formed of a rod-shaped, insertable portion 1 and front holder part 2, as well as holder body 4, and a 3-D image display unit 5'. The rod-shaped, insertable portion 1 has a diameter small enough to be inserted within a living human being and is affixed to the front holder part 2. The insertable portion 1 is provided with an optical system for capturing images having parallax. The image input device 3 includes a pupil-separation-type, rigid endoscope that forms the rod-shaped, insertable portion 1, and the front holder part 2 includes a TV camera. A light source LS, TV camera control unit CU, image conversion computer PC, and a 3-D image observation unit 5' are supported by a cart that forms the holder body 4. As shown in FIG. 16, 3-D observation glasses 10, 11 are provided. The 3-D observation glasses 10 are formed of right and left lenses that transmit different polarization components, respectively. Displayed right and left images having parallax can thus be viewed on the 3-D image observation unit 5' as 3-D images using the observation glasses 10.

Alternatively, 3-D observation glasses 11 may be connected to the image conversion computer PC. This enables 3-D images to be observed when the computer PC sends right and left images of different polarizations to the right and left lenses. The optical observation device of Embodiment 4 is provided with a parallax magnitude conversion system, which will be described in detail below, and is capable of increasing or decreasing the parallax magnitude.

Figure 17:
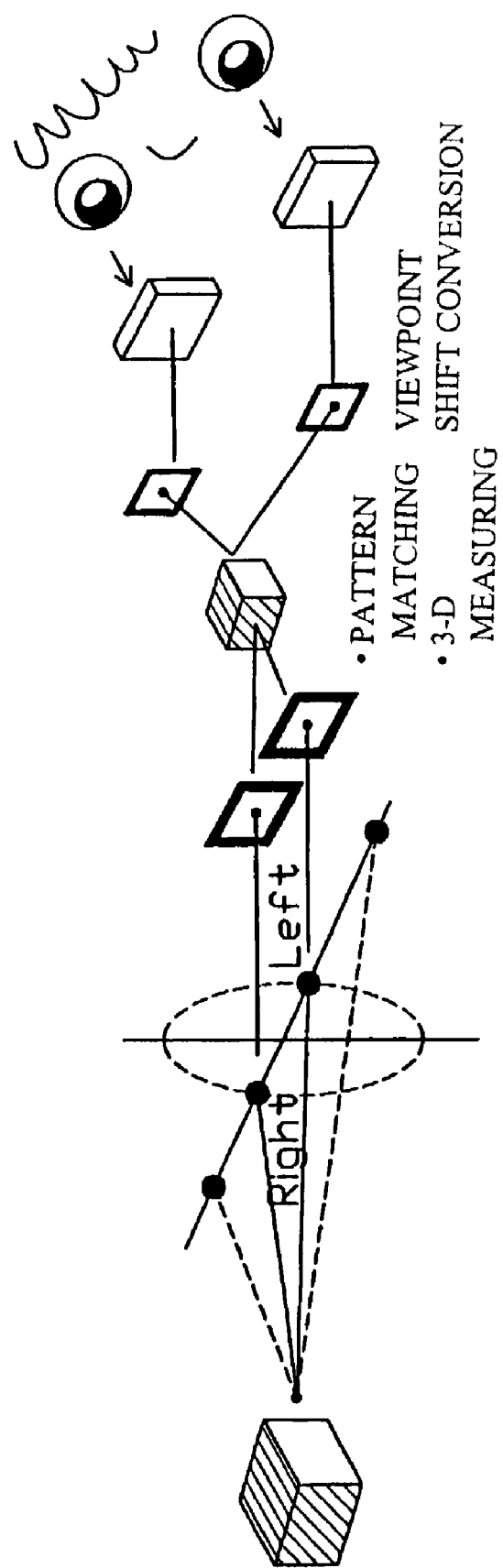
FIG. 17 is a schematic diagram of the parallax magnitude conversion apparatus used in the optical observation device of Embodiment 4 of the present invention.

FIG. 17 is a schematic diagram of a parallax magnitude conversion system used in the optical observation device of Embodiment 4. The parallax magnitude conversion device is similar in operation to the viewpoint shift device. In both devices, right and left images are shifted. Therefore, the corresponding points of the right and left images in the scanning line direction are detected and a calculation is performed to obtain a positional shift magnitude, expressed in pixels, of the right and left images. Performing this for all pixels, the positional shift map of the right and left images is obtained. When the distance between the right and left optical axes is known, a concave-convex magnitude is calculated from the positional shift magnitude. At this point, a 3-D map of the object is produced. Because the coordinate to which the parallax is converted is known (for instance, the parallax magnitude is doubled in this case), projecting onto the coordinate as seen from that direction results in a conversion to 3-D images as seen from a different viewpoint.

In Embodiment 4, the image shift magnitude of the right and left images can be obtained during the parallax magnitude conversion process. The parallax magnitude conversion coefficients can be changed and the converted image viewpoint can be successively renewed, based on the image shift magnitude. This allows an observation with an appropriate parallax magnitude to be maintained on the observation device. The image input optical system 3 of Embodiment 4 (FIG. 16) is formed of the following components: two objective optical systems with image sensor elements similar to that shown in FIG. 15(a). The image input optical system 3 can instead be formed of the two prior-art relay optical systems shown in FIG. 19. The latter construction is useful where the parallax is excessively large due to observing an object that is nearby. In either case, a parallax magnitude conversion device is provided by the computer within holder body 4, as shown in FIG. 16.

The invention being thus described, it will be obvious that the same may be varied in many ways. For example, for larger incident angles of about 60 degrees or more, it is possible to create a polarization membrane that acts on the p and s-components in the opposite way to that described above. Just as before, however, the polarization membrane serves to combine two light paths into a single common path that carries images having different polarizations, with the s-component light being light that has entered via one path, and the p-component light being light that has entered via the other path. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An optical observation device for observing 3-D images of an endoscope, said optical observation device comprising:

an image input means having a rod-shaped front part witH a sufficiently small diameter for insertion within a living human being, the rod-shaped front part containing a front optical system having two separate light paths for capturing images having parallax in a direction that includes a component in the longitudinal direction of the rod-shaped front part; and a relay optical system;

wherein said two separate light paths are obliquely or perpendicularly arranged relative to the longitudinal direction of the rod-shaped front part so that said two senarate light paths are not parallel to the longitudinal direction of the rod-shaped front part, and are combined by a separation surface into one light path which passes through the relay optical system;

an image conversion means for changing the parallax direction of images received from the image input means so as to form converted images;

a 3-D image observation means for enabling the 3-D observation of the converted images; and the image conversion means changes the parallax direction by
(a) using pattern matching, calculating a position shift map in a certain 3-D coordinate system of right and left images captured by the front optical system;
(b) calculating an object point by using 3-D coordinates of two points that correspond to one object in the position shift map; and
(c) projecting the object point onto two points that are positioned on a line that lies in a different direction of the line formed by connecting the two corresponding points.

2. The optical observation device according to claim 1, wherein the image conversion means changes the parallax magnitude by
(a) using pattern matching, calculating a position shift map, in a certain 3-D coordinate system, of right and left images captured by the front optical system;
(b) calculating an object point by using 3-D coordinates of two points that correspond to one object in the position shift map; and
(c) projecting the object point onto two points that are positioned on a line that lies in the same direction as a line formed by connecting the two corresponding points but are spaced apart a different distance than the two corresponding points.

3. The optical observation device as set forth in claim 2, wherein said image conversion means changes the parallax magnitude of the images received from the front optical system when forming the converted images.

4. The optical observation device according to claim 3, wherein:
the image conversion means is capable of increasing or decreasing the parallax magnitude of the converted images.

5. The optical observation device according to claim 4, wherein:
the image conversion means changes the parallax magnitude of the converted images according to coefficients that are input to said optical observation device.

6. The optical observation device according to claim 3, wherein the image conversion means also changes the parallax direction of images received from the image input means.

7. The optical observation device according to claim 2, and further comprising:
a holder body that supports a CCD and is detachably attachable to the image input means having a rod-shaped front part with a sufficiently small diameter for insertion within a living human being; and
a microscope image input means which may be attached to the holder body when the image input means having a rod-shaped front part is detached from the holder body.

8. The optical observation device according to claim 2, and further comprising:
a means for detecting at least one of the parallax direction or parallax magnitude of the front optical system.

9. The optical observation device according to claim 8, wherein:
the parallax direction of the front optical system is detected by the means for detecting and is converted by the image conversion means to correspond to the parallax direction of the 3-D image observation means.

10. The optical observation device according to claim 8, wherein:
the means for detecting measures the parallax magnitude of the images received from the front optical system; and
the parallax magnitude that is measured by the means for detecting is used to change a conversion ratio for the parallax magnitude of images displayed on the 3-D display observation device.

11. The optical observation device according to claim 2, the image conversion means further comprising:
means for producing a 3-D map of the object based on the images having different parallax obtained by the image input means; and
means for obtaining a converted 3-D image from a different viewpoint of the object than that of the image input means.

12. An optical observation device for observing 3-D images of an endoscope, said optical observation device comprising:
an image input means having a rod-shaped front part with a sufficiently small diameter for insertion within a living human being, the rod-shaped front part containing a front optical system having two separate light paths for capturing images having parallax in a direction that includes a component in the longitudinal direction of the rod-shaped front part; and
a relay optical system:
wherein
said two separate light paths are combined into one light path which passes through the relay optical system:
an image conversion means for changing the parallax direction of images received from the image input means so as to form converted images:
a 3-D image observation means for enabling the 3-D observation of the converted images; and
the image conversion means changes the parallax direction by
(a) using pattern matching, calculating a position shift map in a certain 3-D coordinate system of right and left images captured by the front optical system;
(b) calculating an object point by using 3-D coordinates of two points that correspond to one object in the position shift map; and
(c) projecting the object point onto two points that are positioned on a line that lies in a different direction of the line formed by connecting the two corresponding points;
the front optical system includes
a separation surface,
a light receiving surface, and
a reflection surface arranged in each of the two light paths at a front side of a point where the two light paths are combined;
the image input means includes a housing which accommodates the relay optical system;
the two light paths are obliquely arranged relative to the longitudinal direction of the rod-shaped front part and are combined by the separation surface;
the light receiving surface is positioned inside an outer surface of the housing; and
light that travels on each of the two light paths is reflected at least once before being combined by the separation surface.

13. The optical observation device as set forth in claim 12, wherein
the separation surface is a polarization surface that transmits a first polarized light component and reflects a second polarized light component that has its plane of vibration perpendicular to the plane of vibration of the first polarized light component;

the two light paths carry images of different parallax, said two light paths being combined by the polarization surface into a single optical path; and the optical axes of said two light paths, as each optical axis transits an optical input surface of the image input means, are separated and are parallel to each other.

14. The optical observation device as set forth in claim 13, and further comprising:

a prism optical system;

an optical member having two negative lens elements integrally formed thereon, with each negative lens element being axially aligned with a respective one of the separated, parallel optical paths.

* * * * *